United States Patent [19]
Schneider

[11] Patent Number: 4,589,185
[45] Date of Patent: May 20, 1986

[54] ACCESS PORT FORMING METHOD
[75] Inventor: Barry L. Schneider, Deerfield, Ill.
[73] Assignee: Hollister Incorporated, Libertyville, Ill.
[21] Appl. No.: 700,300
[22] Filed: Feb. 11, 1985

Related U.S. Application Data
[62] Division of Ser. No. 458,313, Jan. 17, 1983, Pat. No. 4,530,525.

[51] Int. Cl.⁴ .............................................. B23P 11/00
[52] U.S. Cl. ..................................................... 29/432
[58] Field of Search ............... 604/278, 333, 334, 344, 604/355; 29/432, 526 R

[56] References Cited
U.S. PATENT DOCUMENTS
3,893,446  7/1975  Miller .................................. 604/278
4,050,461  9/1977  Ruby .................................. 604/333

Primary Examiner—Howard N. Goldberg
Assistant Examiner—Steven Nichols
Attorney, Agent, or Firm—Tilton, Fallon, Lungmus

[57] ABSTRACT

A device and method for use in forming an access port, and also in forming a leakproof seal between a conduit (e.g., a catheter tube) and a thermoplastic film (e.g., the wall of an ostomy bag, wound cover pouch, or similar pouch). The device includes internal and external coupling rings adapted to be locked together with a collar of film material clamped therebetween. An elastomeric nipple has an enlarged proximal end portion similarly clamped between the coupling rings and contributes in forming fluid-tight seal between the parts. The method of use of the device is also disclosed, such method including the insertion of a piercing element into the opening of the internal ring to form a two-piece piercing assembly, followed by the step of utilizing that assembly to pierce a flexible plastic film and form a collar of plastic material about the outer surface of the internal ring.

7 Claims, 15 Drawing Figures

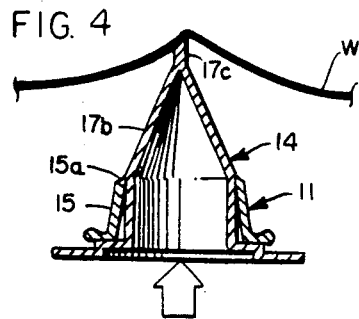
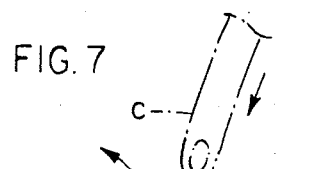
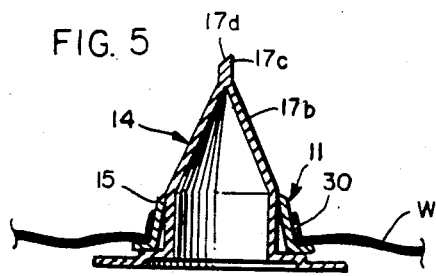
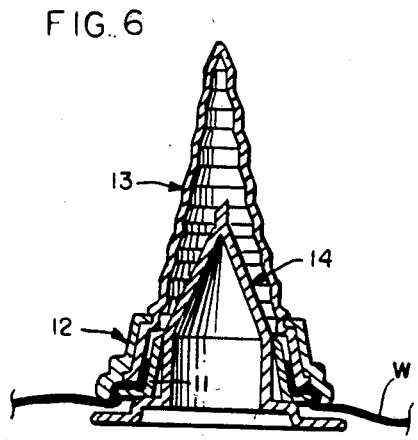
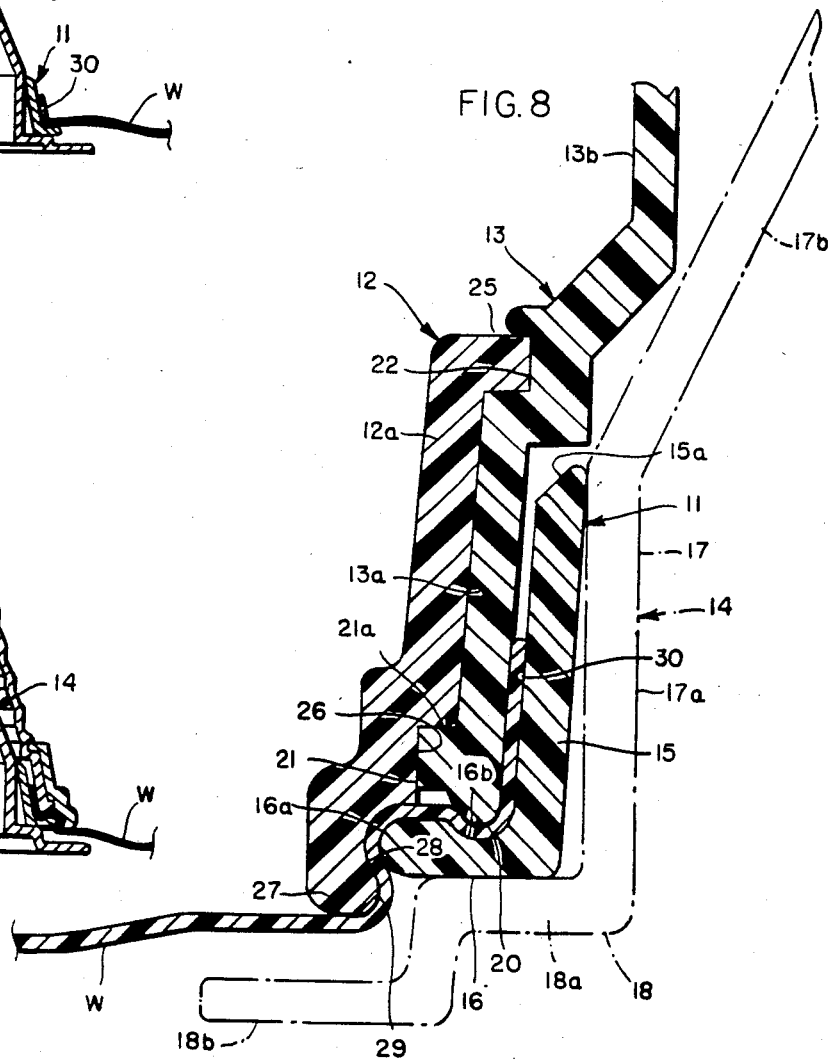

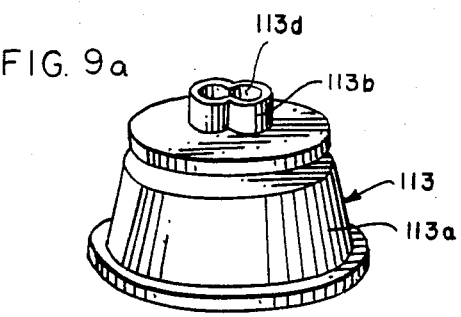
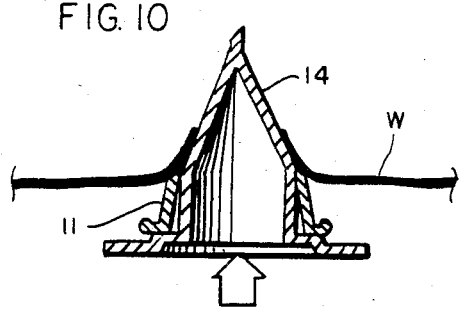
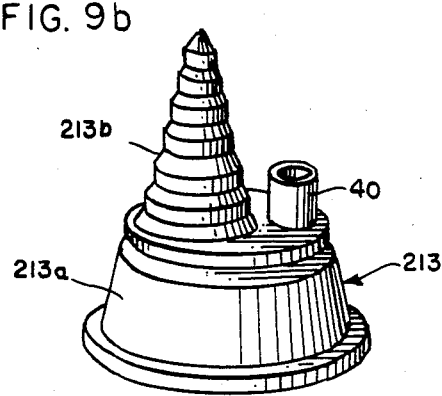
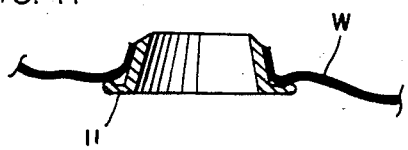
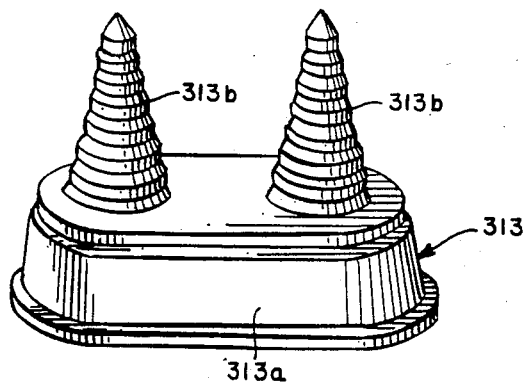
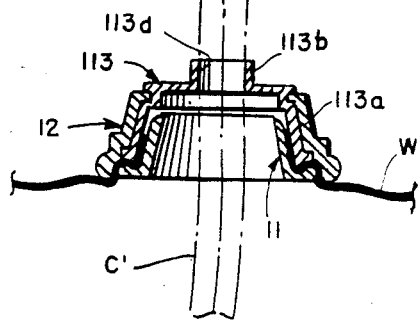
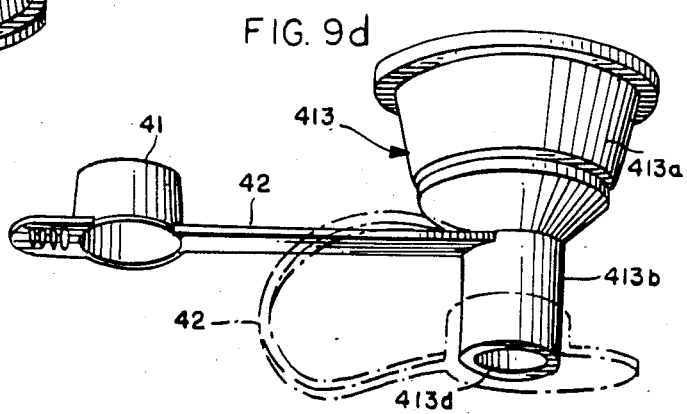

ACCESS PORT FORMING METHOD

This application is a division of application Ser. No. 458,313 filed Jan. 17, 1983, now U.S. Pat. No. 4,530,525.

BACKGROUND AND SUMMARY

U.S. Pat. No. 2,902,036 discloses a disposable ostomy bag having a pre-formed opening 15b through which an internal clamping member 17 may be inserted and then frictionally connected to an outer clamping member 18. The passage through the inner clamping member is sized to provide a fluid-tight seal with the outer surface of a catheter 20 inserted therethrough. A catheter may therefore extend through the wall of the bag without disrupting the integrity of the bag as a fluid collecting device.

Problems associated with such a construction include the need for utilizing a special bag having a pre-formed opening for attachment of the clamping rings and the requirement that only catheter tubes of certain size be used if an effective seal is to be formed between the catheter and the clamping assembly. The latter problem has been reduced in commercial constructions by utilizing a gradually tapered tubular nipple formed of elastic material that may be cut anywhere along its length to form a catheter-receiving opening of selected size. However, in the use of such a product, the nipple is adhesively secured to the wall of a bag after an opening is manually formed therein. Although the use of a bag having a pre-formed single-size opening is eliminated, such a construction introduces additional complexities and problems in manually forming an opening of the proper size in the wall of a bag, insuring that the outer surface of the bag about the opening is dry so that an effective adhesive seal may be formed, adhering the nipple to that outer surface, and preferably framing the area of adhesive attachment with waterproof tape to reduce the possibilities of fluid leakage and/or detachment. Even when such precautions are taken, the possibility remains that separation along the area of adhesive attachment may occur during use.

Other patents illustrative of the state of the art are U.S. Pat. Nos. 3,893,446, 3,830,235, and 4,084,590.

Accordingly, it is an object of this invention to provide a port forming device and method which may be used with flexible thermoplastic films and, in particular, with the film materials commonly used for wound covers, surgical covers, and pouches of the type widely available as collection appliances, and which result in a secure and highly effective leakproof attachment that dispenses with the use of adhesives and sealing agents.

Another aspect of this invention lies in providing a device and method for easily and quickly piercing an access hole in the wall of a flexible plastic film, utilizing an internal coupling ring as an element in the piercing operation, and thereafter joining an external coupling ring to the internal ring to form a fluid-tight seal with the film material. In that connection, it is a specific object and aspect of the invention to interconnect an elastomeric nipple with the external coupling ring so that when the rings are locked together the skirt portion of the nipple is not only securely anchored in place but also functions as a resilient sealing gasket between the parts and as means for absorbing shocks, preventing or reducing kinking, and, in general, stabilizing the connection between the catheter or other conduit and the plastic film through which that conduit extends.

Briefly, the access device includes an internal support ring (or coupling ring) having a side wall with an outwardly-projecting annular flange at one end thereof, a pointed piercing element with a textured surface adapted to be inserted into the support ring to form a wall-piercing assembly with that ring, a tubular nipple of elastomeric material having a proximal end dimensioned to fit about the side wall of the internal support ring and an external locking ring (or coupling ring) dimensioned to receive the side wall of the internal support ring to clamp the proximal end of the nipple, as well as the collar of thermoplastic film, between the internal and external rings, thereby securing the rings and nipple to each other, and to the pierced film, and also utilizing the elastomeric material of the nipple to provide a leakproof seal between the access device and the film. When fully assembled, the components of the access device (excluding the piercing element) latch or lock together to resist disengagement from each other and from the thermoplastic film.

In one embodiment, the tubular nipple is tapered from an enlarged proximal end to a reduced distal end, the taper preferably being incremental and composed of concentric cylindrical sections of progressively decreasing size. By cutting the nipple at a selected location along its length, the cylindrical section of smallest diameter will provide a substantial inner surface for making fluidtight sealing engagement with the outer surface of a catheter tube or other conduit.

Other features, objects, and advantages of the invention will become apparent from the specification and drawings.

DRAWINGS

FIG. 4 is a sectional side view illustrating commencement of a film-piercing operation.

FIG. 5 is a sectional view similar to FIG. 4 but illustrating the parts upon completion of a film-piercing operation.

FIG. 6 is a sectional view showing the subsequent step of coupling the external locking ring and nipple to the internal support ring and pierced thermoplastic film.

FIG. 7 is a sectional view similar to FIG. 6 but depicting the parts following attachment of the access device and after removal of the piercing element.

FIG. 8 is an enlarged fragmentary sectional view illustrating the locking relationship between the parts of a completed assembly.

FIGS. 9a, 9b, 9c and 9d illustrate four alternative nipple configurations that may be used in the method and device of this invention.

FIGS. 10, 11 and 12 illustrate variations in the steps of the method when using a nipple of the type exemplified by FIG. 9a.

DETAILED DESCRIPTION

Figure 1:
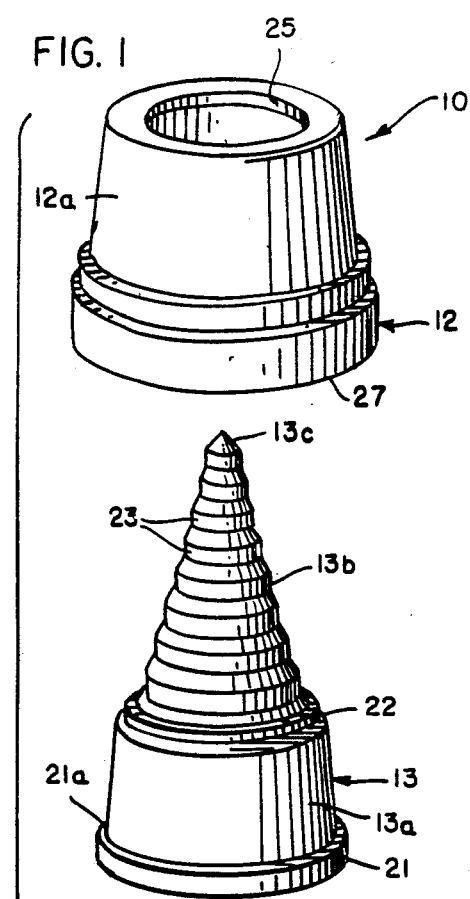
FIG. 1 is an exploded perspective view illustrating the components of an access port forming device embodying this invention.

The port forming device 10 of this invention has three primary components: an internal support ring or coupling ring 11, an external locking ring or coupling ring 12, and an elastomeric nipple 13. A further component, a piercing element 14, is used in piercing the plastic film of a pouch (or other article) and coupling other parts thereto, after which it is removed and may be discarded. To the extent that the coupling rings and nipple become permanently affixed to the film or sheet, that film or sheet also becomes a component of the final combination.

While this device may be used to form an access port in, and a sealing connection with, any suitable film or sheet material, it is especially useful for forming an access port in the wall of a thermoplastic pouch for the purpose of inserting a catheter or other conduit therethrough. The term "pouch" is used herein to mean any protective or collective pouch having an opening adapted to be secured about a wound or stoma for protecting the patient and for collecting exudate. Reference may be had to co-owned U.S. Pat. Nos. 3,954,105, Re. 29,319, 4,203,445, and 4,213,458 for disclosures of various pouches intended for such purposes. The dimensions and constructions of such pouches vary depending on the precise uses for which they are intended; however, such pouches are typically formed of flexible thermoplastic sheet materials composed or treated to provide vapor barrier properties as well as liquid barrier properties. For example, one commercial material comprises low density polyethylene coextruded with a polyvinylidene chloride core, is commercially available under the trademark "Saranex" from Dow Chemical, Midland, Mich. It is to be understood, of course, that the panels of such a pouch may be formed from any of a variety of other suitable thermoplastic materials having similar properties.

The coupling rings 11, 12 and piercing element 14 are formed of a tough, durable, and relatively rigid polymeric material such as high-density polyethylene or polypropylene, although other materials might be used. The internal support ring 11 has a preferably slightly tapered side wall 15 open at opposite ends and provided with an outwardly-projecting annular flange 16 at its proximal end (its lower end, when viewed as depicted). In the embodiment of FIGS. 1-8, the ring is generally cylindrical with a slight upward or distal taper. The outermost surface 16a of the flange is preferably rounded, and the upper surface of the flange (i.e., the surface facing towards the ring's opposite end), is provided with an annular channel or groove 16b (FIG. 8). It will be noted that at its upper or reduced distal end, the internal support ring is provided with a downwardly and outwardly inclined or beveled surface 15a (FIG. 8).

Figure 3:
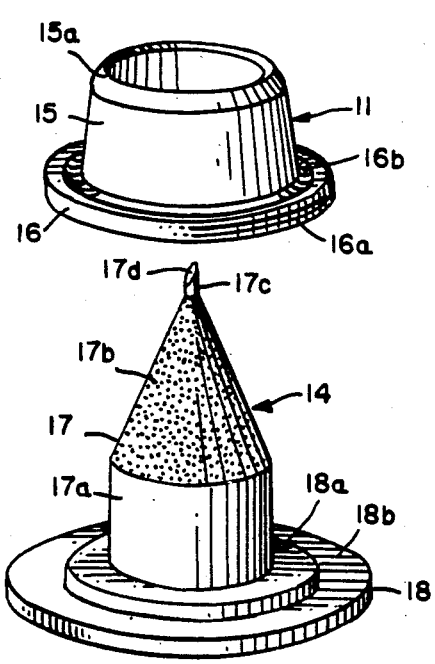
FIG. 3 is a perspective view illustrating the internal support ring and piercing element in preassembled condition.
Figure 3:
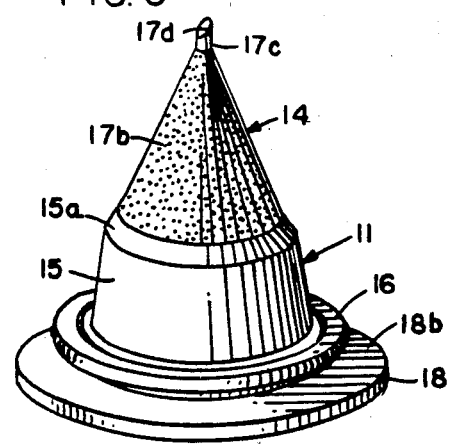

The piercing element 14 has a body portion 17 and a flange portion 18. The body portion 17 includes a cylindrical section 17a of a length approximating the axial dimension of internal support ring 11 and a diameter matching, or slightly greater than, the smallest inside diameter of ring 11. As a result, when the body portion of the piercing element is inserted into the opening of ring 11, the outer surface of cylindrical section 17a will frictionally engage the internal surface of the ring adjacent upper end 15a (FIG. 8). Consequently, when the parts are fitted together as illustrated in FIG. 3, they will remain in connected condition unless sufficient force is exerted to overcome the frictional resistance in the area of contact near beveled end 15a. As already indicated, the wall 15 of the internal support ring 11 is preferably tapered, one purpose being to provide only limited frictional engagement between piercing element 14 and support ring 11 so that excessive force will not be necessary to separate the parts following piercing and coupling operations as described hereinafter. Another purpose for tapering the wall of the ring is to define the shape of the collar of film or sheet material formed over it, so that the collar may be readily captured between the rings.

The body portion 17 of the piercing element 14 also includes a conical upper portion 17b terminating in a beveled blade-like tip 17c. FIGS. 3 and 8 reveal that when the ring 11 and element 14 are preassembled, the sloping end surface 15a of the ring serves as a continuation of, or at least avoids sharp departure from, the sloping outer surface of conical section 17b.

It is to be noted from FIG. 1 that the outer surface of the conical upper portion 17b is textured, in contrast to being polished, glossy, slick, or exceptionally smooth. The texturing may take the form of dense craters and projections of microscopic size that give the surface what is commonly known as a frosted finish, or the texturing may be more substantial, taking the form of surface undulations (of either regular or random pattern) that may be readily discerned by the naked eye. A frosted finish formed by texturing the mold used for forming the piercing element has been found particularly effective, but other texturing techniques may be used. The purpose in any event is to prevent the conical surface of upper portion 17b from sticking to the collar of thermoplastic film or sheet material as that collar is being formed, creating a resistance to sliding movement that exceeds the tear strength of the film or sheet material.

Tip 17c takes the form of a small-diameter cylindrical extension of the conical upper portion 17b having a beveled end surface 17d (FIG. 1). The bevel results in a sharpened piercing edge that is easily urged into and through a film or sheet to initiate collar formation. It has been found that the heel or beveled surface 17d should either merge with the conical surface 17b or should be in close proximity to that surface, so that immediately following the piercing of an opening through a film or sheet, the opening so formed is forced to become enlarged and to develop the characteristic collar, as hereinafter explained.

The annular flange portion 18 of the piercing element includes inner and outer sections 18a and 18b, respectively. Inner section 18a has a diameter less than the outside diameter of the flange 16 of ring 11. The integral outer section 18b is stepped below section 18a and preferably has an outside diameter substantially larger than ring flange 16 and extension 27 to facilitate insertion and removal of the piercing element with respect to internal support ring 11 and external locking ring 13.

Nipple 13 is formed of thermoplastic rubber, latex, or any other suitable elastomeric material, and includes a proximal skirt portion 13a and a tapered distal portion 13b. In the embodiment illustrated in FIGS. 1-8, the skirt portion is generally cylindrical, preferably having a slight taper corresponding with the taper of ring 11 and, in and unstretched state, has inside dimensions approximately the same as, or slightly larger than, the outer surface of the ring's side wall portion 15 (FIG. 8). An annular bead 20 of rounded cross-sectional configuration projects downwardly from the skirt about the open lower end thereof, and is dimensioned to be received within the annular channel or groove 16b of ring flange 16. An external rib 21 extends about the nipple's lower end and provides an upwardly facing shoulder 21a for locking engagement with external ring 12. An annular external recess 22 extends about the skirt portion 13a at the upper end thereof, and is similarly adapted for interlocking engagement with the external coupling ring 12.

The upper portion 13b of the nipple of the form depicted in FIGS. 1–8 progressively diminishes in internal and external dimensions, the taper being incremental rather than smooth or uninterrupted. Specifically, the upper portion is stepped to provide a plurality of coaxial cylindrical wall portions 23 of incrementally diminishing size in an upwardly-extending series. Such cylindrical wall portions 23 have generally cylindrical inner surfaces of incrementally diminishing size, the sizes corresponding generally to the range of catheter sizes that might be used with the assembly. In the illustration given, the nipple is closed at its upper end 13c, although it may, if desired, be supplied to the user with an opening having a diameter corresponding to the inside diameter of the smallest cylindrical portion 23 of the series.

The external locking ring 12 has a side wall 12a whose internal surface conforms generally with the outer surface contour of the skirt portion 13a of nipple 13. Specifically, the external locking ring has an inwardly-projecting annular flange or rib 25 adapted to be received within external recess 22 of the nipple's skirt portion 13a (FIG. 8). An internal annular indentation 26 near the lower end of the skirt portion receives rib 21 at the lower end of the nipple. In addition, the external locking ring includes a downwardly-extending annular extension 27 that continues downwardly beyond the nipple's skirt portion (when the parts are assembled as shown in FIG. 8) and is provided with an annular internal channel 28 for receiving the rounded periphery of flange 16 of internal support ring 11. Extension 27 projects below flange 16 and also inwardly beneath that flange, defining an opening at the lower end of ring 12 that is smaller than the maximum diameter of channel 28 and the outside diameter of flange 16a. Therefore, when the parts are assembled as depicted in FIG. 8, a snap fit develops between flange 16 and the internally-grooved extension 27 to resist subsequent axial separation of the parts.

Figure 2:
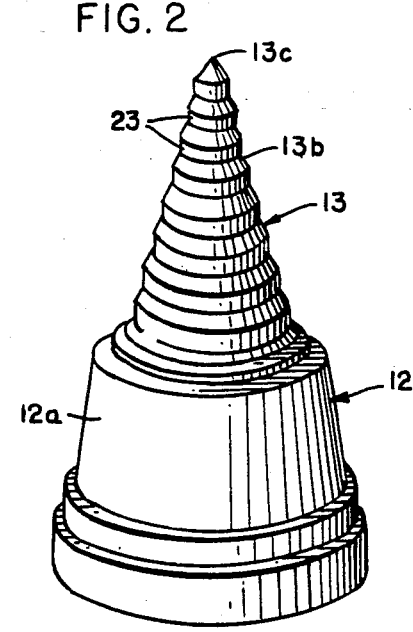
FIG. 2 is a perspective view showing the external locking ring and tubular nipple in preassembled condition.

The steps of using the device of FIGS. 1–3 are illustrated in FIGS. 4–7. Assuming that the piercing element 14 and internal support ring 11 are not supplied in preassembled form, the user first joins such parts as shown in FIG. 3 and then directs the pointed tip of the piercing element into and through flexible wall W as represented in FIGS. 4 and 5. The action is essentially a piercing and drawing operation rather than a cutting operation, with the result that as an opening develops in the wall and is enlarged by advancement of the textured, conical piercing element (and the internal ring 11 carried by it), the material of the wall folds upwardly to form an upwardly-projecting collar 30 that tightly encircles wall 15 of the internal support ring when the piercing and drawing step is completed (FIG. 5). Although the piercing operation is initiated by the beveled tip of the piercing element 14, and becomes a stretching and enlarging operation as the conical surface 17b progresses through the opening in the wall, a transition occurs near the end of the piercing and stretching steps, with collar 30 being directed from conical portion 17b onto the generally cylindrical wall 15 of ring 11. The beveled end surface 15a of the ring helps insure a smooth transfer of collar 30 from the conical surface of the piercing element to the outer surface of ring 11.

The outer locking ring 12 and nipple 13 are preassembled, as shown in FIG. 2, either by the manufacturer or the user. The assembly is fitted over the protruding conical portion of piercing element 14, and snapped about the flange of inner support ring 11, in the manner depicted in FIGS. 6 and 8. As the subassemblies are brought together, the material of wall W is directed about flange 16 of the internal support ring and is formed into the annular groove 16b provided by that flange. With the external locking ring snapped in place, the thermoplastic wall is firmly clamped between the rounded outer surface 16a of flange 16 and the curved inner surface of channel 28. In addition, the skirt portion 13a of the resilient, elastomeric nipple 13 is held in tight sealing engagement with the collar 30 of the wall W and with that portion of the wall received within annular groove 16b. The result is that the wall, coupling rings, and nipple are not only immobilized with respect to each other, but the resilient skirt of the nipple is utilized to insure a fluid (and gas) tight seal between such parts.

Following the coupling operation, piercing element 14 is simply withdrawn from the internal ring 11, and the stepped end portion of the nipple is cut transversely to expose a cylindrical opening of a size that will slidably and sealingly engage the outer surface of a selected catheter C (or other conduit or conductor). Although the tip of the catheter might be inserted through the nipple opening in the direction shown in FIG. 7, it is generally easier to draw the catheter upwardly through the nipple in a reverse direction. A suitable lubricant may be applied to the nipple and/or catheter to facilitate such insertion.

FIGS. 9a through 9d depict certain variations in nipple construction and configuration for use with modified procedures and equipment. Thus, in a case where the catheter or other conduit with which the assembly is to be used is of a specialized size and configuration, as where the catheter is a multi-lumen catheter of a distinctive non-circular cross sectional outline, the elastomeric nipple may assume the shape illustrated in FIG. 9a. Skirt portion 113a of nipple 113 is preferably slightly tapered to fit between internal and external rings 11 and 12, respectively. Instead of having an elongated, tapered distal portion as in the preceding embodiment, nipple 113 has a reduced distal portion 113b with a non-circular opening 113d dimensioned for sealingly but adjustably receiving a plural-lumen catheter of non-circular external shape.

The elastomeric tubular nipple 113 cooperates with the internal support ring 11 and external locking ring 12, and with film W, in the same manner already described except for one difference in operating procedure. Because of the relatively short axial length of nipple 113, piercing element 14 must be withdrawn from the internal support ring 11 after the film W is pierced and before the external ring 12, with nipple 113 coupled thereto, is secured in place. The sequence is indicated in FIGS. 10–12 where it will be seen that the film is first pierced (FIG. 10) as already described but then, before coupling the internal and external rings together with the film W and skirt 113a clamped therebetween, the piercing element 14 is separated from the internal support ring 11 (FIG. 11). Thereafter, the external ring 12, preassembled with nipple 113, is coupled to the internal support ring 11 (FIG. 12). With the coupling completed, the plural-lumen catheter C' may be inserted through the opening 113d of the elastomeric nipple with a fluid-tight seal preferably being formed between the outer surface of the catheter and the inner surface of the nipple within opening 113d.

Whether the piercing element 14 remains attached to internal support ring 11 during the coupling step depends partly on the relative axial dimensions of the piercing element and the nipple and partly on the preferences of the user. In general, it is advantageous to keep the piercing element attached to the internal ring until after the internal and external rings have been snapped together (with the film material W and the skirt of the nipple clamped therebetween) if the axial dimension of the nipple, at least in a stretched state, is sufficient to accommodate the tapered portion of the piercing element 14. However, there may be instances in which a user would find it preferable to separate the piercing element from the internal ring prior to the coupling step even if the internal dimensions of the nipple were large enough to accommodate the tapered portion of the piercing element. For example, FIG. 6 has been described in connection with a procedure in which piercing element 14 is not separated from internal support ring 11 until after external locking ring 12 is snapped into the position shown. While such a procedure represents the preferred method of operation, it is to be understood that even though nipple 13 is large enough to accommodate the tapered portion of the to detach the piercing element 14 from the internal support ring 11 after the piercing operation of FIGS. 4 and 5 is completed and before the internal and external rings are coupled together.

FIGS. 9b, 9c, and 9d show further variations of the elastomeric nipple suitable for different purposes or applications. Nipple 213 of FIG. 9b is basically the same as nipple 13 of FIG. 1 except that the stepped tapered portion 213b is eccentrically located and an integral vent tube 40 is disposed alongside tapered portion 213b. Such a nipple may be used where, in addition to catheter access through tapered portion 213b, it is desirable to insert a suction tube or an irrigation tube through tubular portion 40 of the nipple, or simply to provide a vent opening for the purpose of equalizing pressure during evacuating or irrigating procedures.

FIG. 9c shows a further modification wherein nipple 313 has a pair of stepped and tapered portions 313b to accommodate a pair of catheters or other conduits. The skirt portion 313a of nipple 313 is oval but in other respects is similar to the skirt portions 313a, 213a, and 113a of the previous embodiments. In each embodiment, the skirt portion of the nipple is designed to cooperate with an internal support ring 11, an external locking ring 12, and a wall or film W of plastic material, in the manner illustrated in FIG. 8.

FIG. 9d shows an elastomeric nipple 413 in inverted position for use as a drain tube for a thermoplastic pouch. The nipple may be equipped with a captive cap 41 attached to the nipple by an integral strap 42, the cap being dimensioned to seal the distal portion 413b of the nipple in the manner indicated in broken lines. As with the other embodiments, nipple 413 has a tapered skirt portion 413a which is capable of cooperating with internal and external rings 11 and 12, and with the wall W of the pouch, as previously discussed in connection with FIG. 8.

While in the foregoing, I have disclosed embodiments of the invention in considerable detail for purposes of illustration, it will be understood by those skilled in the art that many of these details may be varied without departing from the spirit and scope of the invention.

I claim:

1. A method of forming an access opening in a wall of thin, flexible, stretchable thermoplastic material comprising the steps in order of placing a coupling ring about the body section of a piercing element having a generally conical portion extending axially beyond said ring; piercing said wall with said conical portion and advancing said element and ring to cause an annular axially-directed collar of stretched material to be positioned externally about said ring; positioning the resilient annular skirt portion of a tubular elastomeric nipple about said ring and collar; and then locking said resilient skirt portion tightly against said collar to seal said collar against both said skirt portion and said ring.

2. The method of claim 1 in which said locking step involves fitting a second coupling ring about said first coupling ring to clamp said skirt portion and collar therebetween.

3. The method of claim 2 in which there is the further step of removing said piercing element from said first coupling ring; said step of removing said piercing element occurring after said locking step.

4. The method of claim 2 in which there is the further step of removing said piercing element from said first locking ring; said removing step occurring after said piercing step and before said positioning step.

5. The method of claim 2 in which said first-mentioned coupling ring includes an outwardly-projecting flange and said second coupling ring is provided with an internal channel adapted to receive an interlock with said flange; said locking step including advancing said coupling rings to cause said flange of said first ring to be received within said channel of said second ring.

6. The method of claim 1 in which said nipple includes a tapered portion extending axially from said skirt portion; said tapered portion including a plurality of coaxial cylindrical wall portions of progressively decreasing diameter; and transversely cutting one of said cylindrical wall portions to provide an opening dimensioned to receive a conduit of selected external diameter.

7. The method of claim 6 in which there is the further step of inserting said conduit through said opening by cutting said nipple to form a tight seal between the inner surface of said cylindrical portion and the outer surface of said conduit.

* * * * *